United States Patent [19]
Malin et al.

[11] Patent Number: 5,643,742
[45] Date of Patent: Jul. 1, 1997

[54] SYSTEM FOR ELECTRONICALLY MONITORING AND RECORDING CELL CULTURES

[75] Inventors: Patricia J. Malin, Palo Alto; Kenneth Richard Wada, Cupertino; Oskar Werner Huber, Belmont, all of Calif.

[73] Assignee: CellStat Technologies, Inc., Belmont, Calif.

[21] Appl. No.: 374,542

[22] PCT Filed: Jul. 29, 1992

[86] PCT No.: PCT/US92/06269

§ 371 Date: Mar. 23, 1995

§ 102(e) Date: Mar. 23, 1995

[87] PCT Pub. No.: WO94/03583

PCT Pub. Date: Feb. 17, 1994

Related U.S. Application Data

[63] Continuation-in-part of Ser. No. 125,507, Sep. 23, 1993, abandoned, which is a continuation of Ser. No. 883,063, May 8, 1992, abandoned, which is a continuation of Ser. No. 503,791, Apr. 3, 1990, abandoned.

[51] Int. Cl.$^6$ ............................. C12Q 1/00; C12M 1/34; C12M 1/42
[52] U.S. Cl. ..................... 435/29; 435/173.1; 435/287.1; 435/288.4; 435/305.3; 324/692
[58] Field of Search ........................... 435/286.1, 287.1, 435/40, 288.4, 29, 34, 39, 305.3, 173.1, 173.8; 422/82.01, 82.02; 204/153.12, 403; 324/439–450, 691, 692; 364/497, 499, 413.1

[56] References Cited

U.S. PATENT DOCUMENTS

| | | |
|---|---|---|
| 3,743,581 | 7/1973 | Cady et al. . |
| 3,770,607 | 11/1973 | Williams .................................. 204/403 |
| 3,890,201 | 6/1975 | Cady . |
| 3,984,766 | 10/1976 | Thornton . |
| 4,072,578 | 2/1978 | Cady et al. . |
| 4,156,180 | 5/1979 | Annen et al. . |
| 4,160,205 | 7/1979 | Hobbs et al. . |
| 4,230,983 | 10/1980 | Steere et al. . |
| 4,262,253 | 4/1981 | Clark ........................................ 324/442 |
| 4,789,635 | 12/1988 | Ackland et al. . |
| 4,808,930 | 2/1989 | Kaiser . |
| 4,972,137 | 11/1990 | Dunstan et al. . |
| 5,001,417 | 3/1991 | Pumphrey ................................ 422/102 |

OTHER PUBLICATIONS

Bailey et al. Biochemical Engineering Fundamentals. McGraw–Hill, Inc. U.S.A. (1986), pp. 684–693.

Glaser, V., "Automation and Process Control Advances in Bioreactor Fermenter Systems," *Genetic Engineering News* 7:33 (1993).

Hoffman, R.A. and Swartzendruber, D.E., "Electrical Impedance Analysis of Single Murine Teratocarcinoma Cells," in *Experimental Cell Research*, vol. 122, No. 2 (Caspersson, T., et al., Eds.), Academic Press, New York, pp. 426–429 (1979).

Leif, R.C., et al., "Electrical Impedance (Coulter Effect) Measurements of Single Human Erythrocytes," in *Abstracts of the Federation Proceedings of the 63rd Annual Meeting of Federation of American Societies for Experimental Biology* 38(3):1062 (1979).

Peters, J.E., et al., "Rapid Detection of Bacterial Growth in Clinical Specimens and Measurement of Lymphocyte Metabolism in Culture by the Electrical Impedance Method," *Abstracts of the Annual Meeting of the Society for Microbiology* (Slepecky, R., et al., Eds.) pp. 62 (1978).

Ur, A., and Brown, D.F.J., "Impedance Monitoring of Bacterial Activity," *J. Med. Microbiology* 8(1):19 (1975).

Cady, P., et al., "Electrical Impedance Measurements: Rapid Method for Detecting and Monitoring Microorganisms," *Journal of Clinical Microbiology* 7: 265–272 (1978).

Giaever, I., and C.R. Keese, "Use of Electric Fields to Monitor the Dynamical Aspect of Cell Behavior in Tissue Culture," *IEEE Transactions on Biomedical Engineering* BME–33 2: 242–247 (1986).

Khan, W.N., et al., "An Electrical Impedance Method for Rapid Measurement of Tumor Cell Sensitivity to Anti–Cancer Drugs," *Drugs Exptl. Clin. Res.* VII(5): 642–647 (1981).

*Primary Examiner*—William H. Beisner
*Attorney, Agent, or Firm*—Charles K. Sholtz; Peter J. Dehlinger

[57] ABSTRACT

This invention provides an improved system for monitoring and recording cell cultures. A method for measuring a delay period for an alternating current voltage applied across a pair of pins improves the stability of measurements made with the improved system. A method for applying a voltage across a pair of pins which avoids exceeding a pre-established voltage avoids the possibility of damaging and/or destroying cells while monitoring their culture.

18 Claims, 4 Drawing Sheets

SYSTEM FOR ELECTRONICALLY MONITORING AND RECORDING CELL CULTURES

This application is a continuation of PCT/US92/06269 filed 29 Jul. 1992, herein incorporated by reference. This application is a continuation-in-part of U.S. patent application Ser. No. 08/125,507, filed 23 Sep. 1993, now abandoned, which is herein incorporated by reference, which is a continuation of U.S. patent application Ser. No. 07/883,063, filed 8 May 1992, now abandoned, which is herein incorporated by reference, which is a continuation of U.S. patent application Ser. No. 07/503,791, filed 3 Apr. 1990, now abandoned, which is herein incorporated by reference.

TECHNICAL FIELD

The present invention relates generally to systems for monitoring the growth of cells while being cultured and, more particularly, to such systems that employ an electrical current for monitoring the culture.

BACKGROUND ART

Patent Cooperation Treaty ("PCT") patent application no. PCT/US91/02320 filed 3 Apr. 1991, published 17 Oct. 1991, and entitled "An Electronic Technique of Identifying an Effective Drug for Treating a Cancer Patient" discloses a system for monitoring and recording cell cultures. This PCT patent application claims priority from a similarly titled U.S. patent application No. 07/503,791 filed 3 Apr. 1990, now abandoned, that discloses a similar cell culture monitoring and recording system.

The system disclosed in these patent applications monitors and records cells being cultured in a conventional laboratory tray. The tray has a plurality of separate wells with each well being open at one end. This system includes a lid that is disposed on top of the tray to cover the open ends of the tray's wells. Secured to the top surface of the lid is a printed circuit board that has a plurality of individual electrically conductive traces formed on one surface. One end of each trace is adapted to mate with and engage a printed circuit board connector. Also secured to each trace is a non-reactive, stainless steel pin that penetrates both the printed circuit board and the lid. The placement of the traces on the printed circuit board with respect to the lid arranges the pins in pairs so that when the lid is placed on the tray each pair of pins is inserted through the open end of and extends into a different well in the tray.

This system also includes a printed circuit board connector that mates with the traces of the printed circuit board and through which one pin of every pair is electrically connected to a common potential. An electronic data acquisition board is electrically coupled to the printed circuit board connector. The electronic data acquisition board includes a voltage source for applying an electrical voltage across a pair of the pins. A plurality of well switches, also included in the electronic data acquisition board, selects one particular pair of the pins to receive the voltage supplied by the voltage source. In operation, the electronic data acquisition board preferably applies an alternating current voltage of approximately 10 millivolts peak-to-peak across the pair of pins. This alternating current voltage preferably has a frequency of approximately 400 Hz that is not harmonically related to 60 Hz. An amplifier, also included in the electronic data acquisition board, has an input that receives the voltage applied across the pair of pins selected by the well switches. From its output, the amplifier transmits a signal that responds to the voltage present at the amplifier's input to a sample-and-hold circuit. The sample-and-hold circuit receives the output signal from the amplifier and, in turn, transmits a signal responsive to that signal.

This cell culture monitoring and recording system also includes a computer system that itself includes a measurement input/output circuit. The measurement input/output circuit includes means for supplying signals to the electronic data acquisition board for specifying a particular pair of pins to be selected by the switches. The measurement input/output circuit also includes an analog-to-digital converter that receives and digitizes the signal from the sample-and-hold amplifier to produce a digital number. For processing these digital numbers, the computer system includes a means for storing them as raw data, and means for analyzing the raw data and graphically displaying the results of such analysis.

While the system disclosed in these patent applications is capable of monitoring and recording cells during culture, certain limitations render the precise embodiment disclosed in the patent applications unsuitable for widespread commercial application. For example, pins made from electrically conductive, non-reactive stainless steel do not always achieve a reliable electrical connection to the traces of the printed circuit board. Thus, occasionally, one or more pairs of pins out of all the pairs in a lid might produce an erratic reading, or no reading at all. Such an intermittent or open circuit condition might occur several hours or days into a test monitoring and recording cell growth, thereby severely reducing or perhaps destroying the usefulness of the test results. Similarly, drift in the electronic components used in the system over several days of a test could introduce instability and/or inaccuracy into measurements recorded by the system. Furthermore, during culture cells may be damaged and/or destroyed if a monitoring system inadvertently applies a voltage, that while being very small, is still excessively large in comparison with biological electrical potentials. Also, the data analysis techniques disclosed in the patent applications identified above did not most effectively reveal the full quality of data obtained with the system.

DISCLOSURE OF INVENTION

An object of the present invention is to provide an improved system for monitoring and recording cell cultures.

Another object of the present invention is to provide a lid for a cell culture monitoring and recording system having more reliable electrical connections between non-reactive pins thereof and electrically conductive traces on a printed circuit board included therein.

Another object of the present invention is to provide a cell culture monitoring and recording system that achieves higher stability.

Another object of the present invention is to provide a cell culture monitoring and recording system that more precisely measures electrical conductivity of cells being cultured.

Another object of the present invention is to provide a cell culture monitoring and recording system that does not harm cells during culture.

Another object of the present invention is to provide a cell culture monitoring and recording system that more effectively presents test results.

Briefly, the present invention includes an improved lid having a plurality of individual pin sockets that are interposed between traces on a printed circuit board and electrically conductive pins that, in use, extend into cell growth media held in wells of a standard laboratory tray. Using such pin sockets provides more reliable electrical connection between the nonreactive, electrically conductive pins and the traces on the printed circuit board.

The improved system also determines a delay period used in measuring electrical conductivity between a pair of pins while applying an alternating current electrical potential across the pair of pins to monitor cell growth. The use of this delay period in measuring electrical conductivity increases measurement stability.

The improved system also initially applies a low, safe voltage across a pair of pins prior to monitoring cell growth, and then successively increases the voltage until reaching a pre-established voltage. This method for applying the pre-established voltage avoids the possibility of exposing the cells to an excessively large electrical potential.

In analyzing recorded cell growth data, the improved system subtracts electrical conductivity measured for a reference well that holds only cell growth media without cells from that measured for wells that hold both cell growth media and cells. By subtracting the electrical conductivity of the reference well from other wells, the improved system more effectively presents the results of monitoring and recording cell cultures.

These and other features, objects and advantages will be understood or apparent to those of ordinary skill in the art from the following detailed description of the preferred embodiment as illustrated in the various drawing figures.

BEST MODE FOR CARRYING OUT THE INVENTION

The following disclosure of improvements in the cell culture monitoring and recording system disclosed in PCT patent application Ser. No. PCT/US91/02320 filed 3 Apr. 1991, published 17 Oct. 1991, and entitled "An Electronic Technique of Identifying an Effective Drug for Treating a Cancer Patient," and in the similarly titled U.S. patent application Ser. No. 07/503,791 filed 3 Apr. 1990, now abandoned, expressly incorporates by reference the disclosures of those two patent applications.

Improved Lid 10

Figure 1:
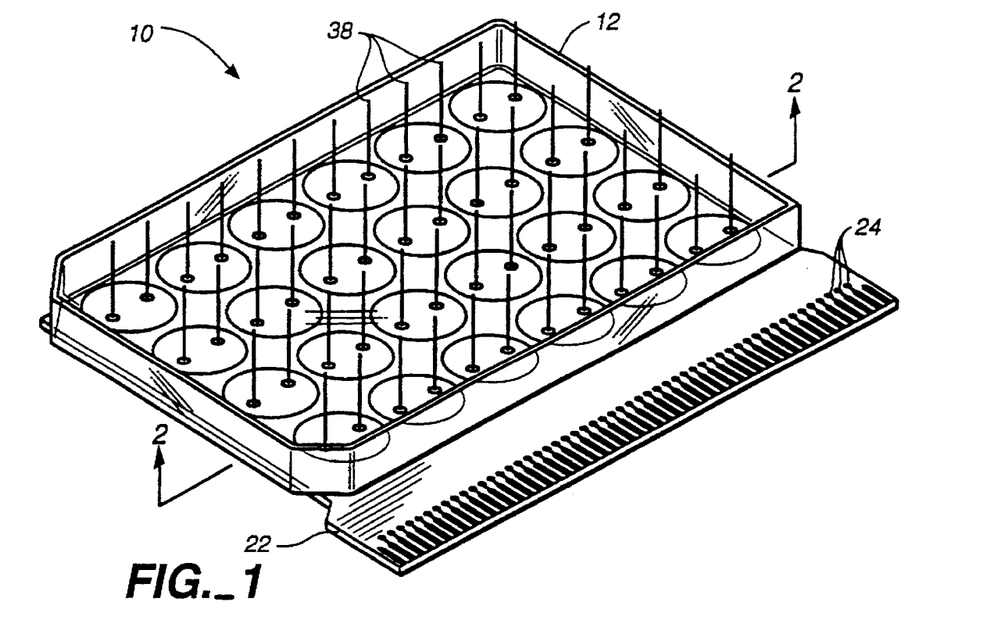
FIG. 1 is a perspective view depicting an improved lid in accordance with the present invention including its cover, pairs of pins, pin sockets and printed circuit board.
Figure 2:
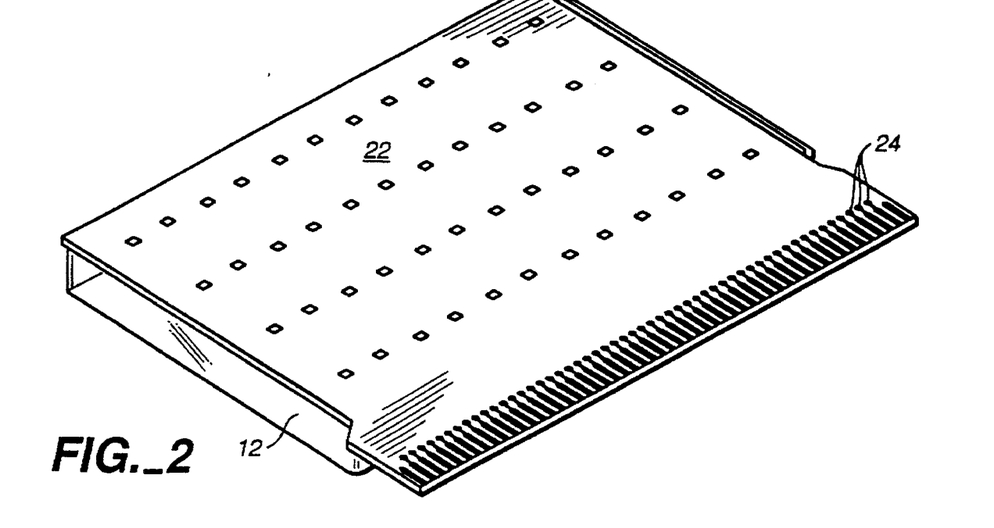
FIG. 2 is a perspective view of the improved lid taken along the line 2—2 of FIG. 1 depicting another view of the printed circuit board and cover thereof.

FIGS. 1 and 2 illustrate alternative views of an improved lid 10 in accordance with the present invention. The lid 10 includes a cover 12 adapted to be positioned over a laboratory tray 14 in the manner illustrated in FIG. 3. The laboratory tray 14 includes a plurality of wells 16, each well 16 having an open end 18. Each of the wells 16 is adapted for holding a quantity of call growth media in which cells may be cultured. When the cover 12 of the lid 10 is positioned over the laboratory tray 14, the cover 12 blocks the open ends 18 of the wells 16.

Referring again to FIGS. 1 and 2, included in the lid 10 is a printed circuit board 22 that is secured to the cover 12. Various alternative techniques may be employed for securing the printed circuit board 22 to the cover 12. For example, machine screws (not illustrated in any of the FIGS.) may extend through matching apertures formed through the printed circuit board 22 and cover 12, the machine screws being secured there by mating nuts threaded thereon (not illustrated in any of the FIGS.). Alternatively, the printed circuit board 22 may be secured to the cover 12 by an adhesive material disposed between their juxtaposed surfaces.

Figure 3:
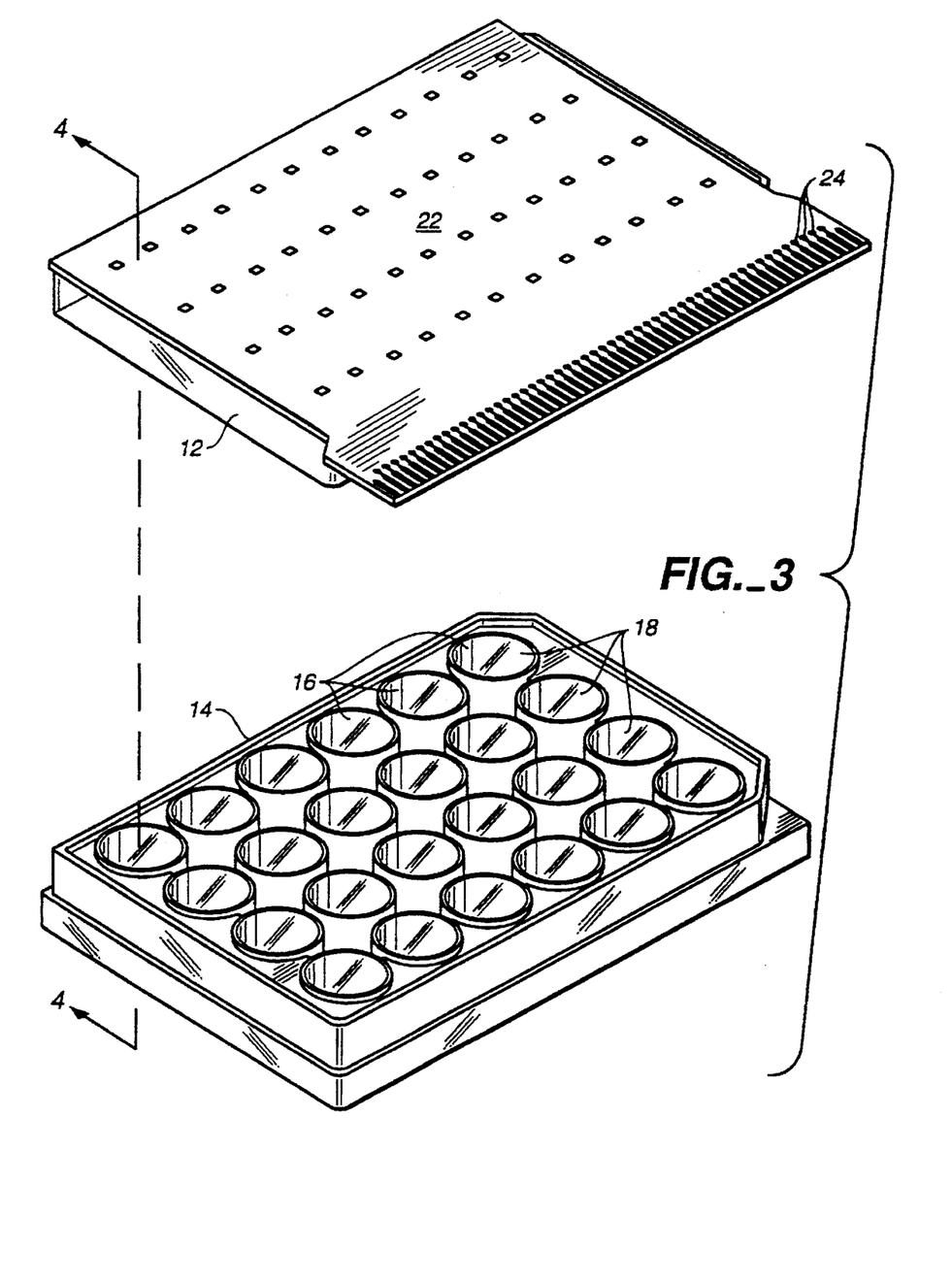
FIG. 3 is a perspective view depicting positioning of the lid of FIG. 2 onto a laboratory tray that has a plurality of wells, each well being adapted for holding a quantity of cell growth media in which cells may be cultured.

The printed circuit board 22 includes a plurality of individual electrically conductive traces 24 formed on its surface as illustrated in FIGS. 1–4. As illustrated in FIG. 1–3, one end of each trace 24 is adapted to mate with and engage a printed circuit board connector (not illustrated in any of the FIGS.). An aperture 26 is formed through the printed circuit board 22 near the other end of each trace 24 to receive a first end 27 of a pin socket 28. The pin sockets 28, preferably model SC 5P1.GG manufactured by Samtec, Inc. of New Albany, Ind., are respectively electrically coupled and secured to the traces 24 by solder 32. A circular aperture 34, formed through the cover 12 concentric with the pin socket 28, receives a second end 36 of the pin socket 28. The second end 36 of each pin socket 28 receives and retains an elongated pin 38 preferably formed from a non-reactive, electrically conductive material such as gold or stainless steel wire 0.508 mm (0.020 inches) in diameter. Each of the pin sockets 28 included in the lid 10 preferably forms a gas-tight seal with the pin 38 inserted thereinto.

Figure 4:
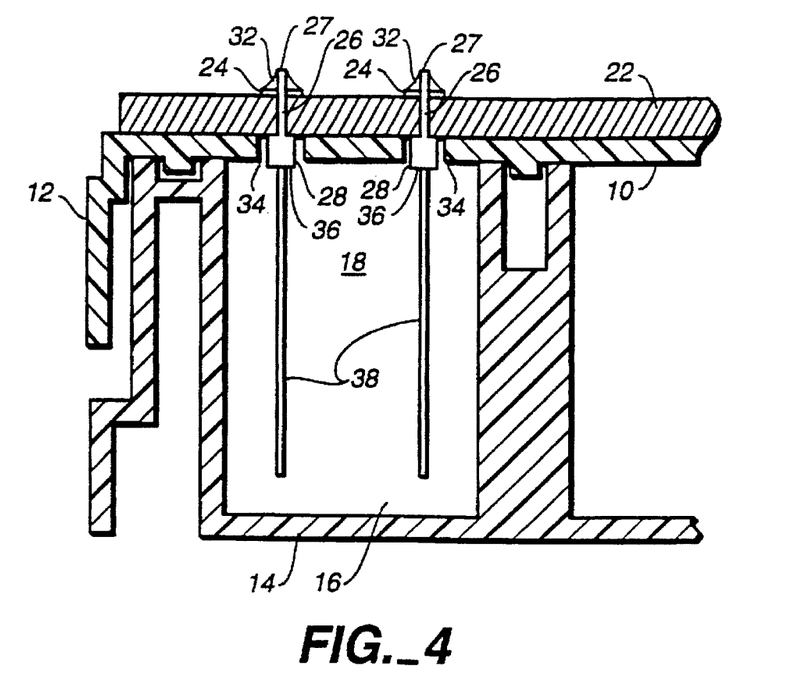
FIG. 4 is a cross-sectional view of a single well in the assembled lid and laboratory tray taken along the line 4—4 of FIG. 3 illustrating a pair of pins, one end of each pin being inserted into and retained in a pin socket.

The placement of the traces 24 on the printed circuit board 22 arranges the pin sockets 28 and pins 38 into pairs. The combined length of each pin socket 28 and the pin 38 received thereinto penetrates both the printed circuit board 22 and the cover 12 with the ends of each pair of pins 38 furthest from the pin socket 28 being insertable through the open end 18 of a well 16 in the laboratory tray 14 when the lid 10 is positioned thereover as illustrated in FIG. 4. So positioning the lid 10 on the laboratory tray 14 disposes each pair of pins 38 so they may extend into cell growth media held in the well 16. However, the end of the pins 38 furthest from the pin sockets 28 must not contact the end of the well 16 furthest from its open end 18, and the quantity of cell growth media held in the well 16 must be sufficiently small that the media does not contact the pin sockets 28.

Before the system may be used to monitor and record cultured cells, the lid 10 must be sterilized so it will not contaminate the cell culture. However, sterilizing the lid 10 must be performed properly to avoid interrupting electrical conductivity between the pins 38 and the traces 24, particularly at the gastight engagement between the pin socket 28 and the pin 38. One procedure that has been successfully applied for sterilizing the lids 10 is to immerse the lid 10 in 70% isopropyl alcohol or ethanol, and then to dry the lid 10 in a laminar flow hood while exposing it to ultraviolet light.

Cell Culture Monitoring Circuit

Figure 5:
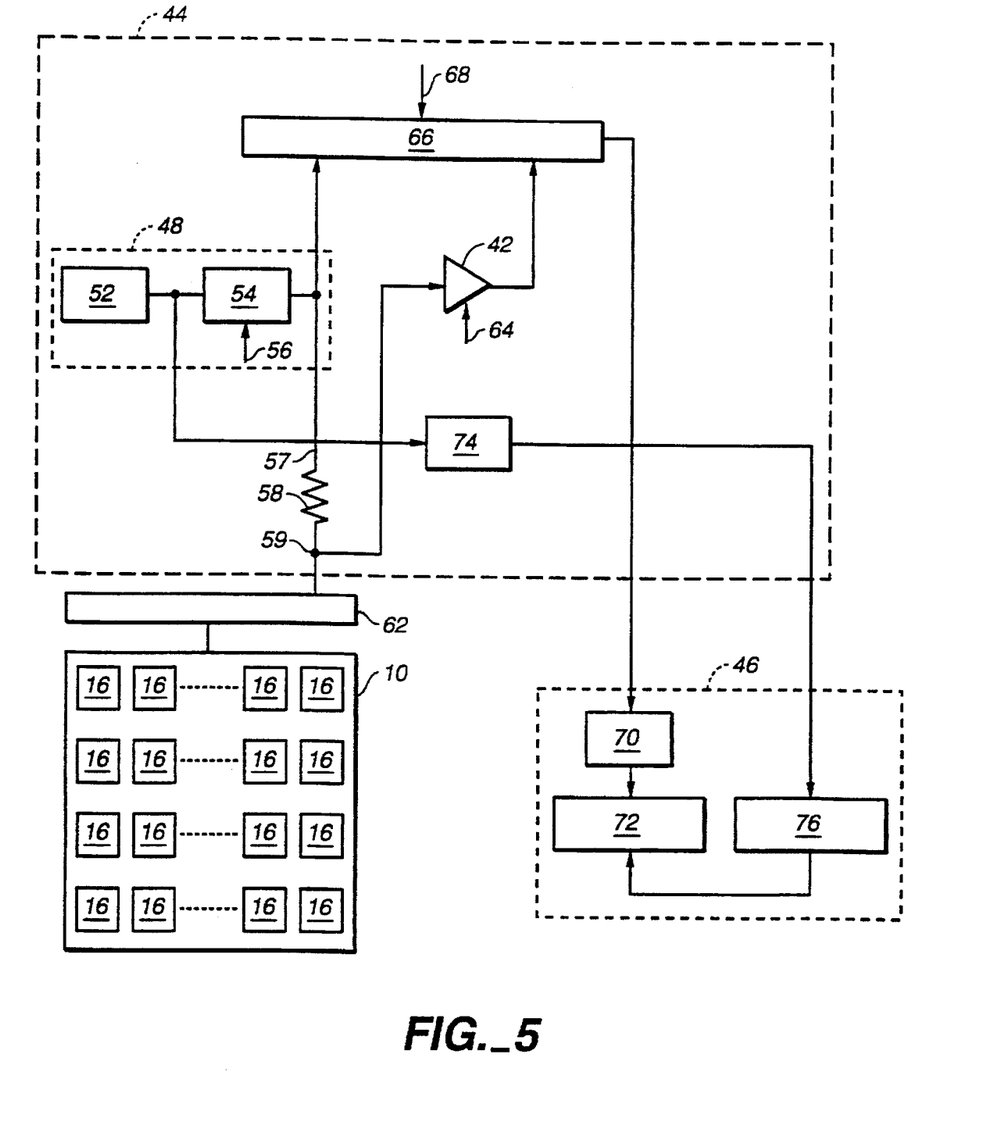
FIG. 5 is a block diagram depicting selected portions of the data acquisition board and of the measurement input/output board in accordance with the present invention.

As disclosed in PCT patent application No. PCT/US91/02320 and in U.S. patent application Ser. No. 07/503,791, now abandoned, the system disclosed in those patent applications monitors a cell culture by briefly applying a low voltage alternating current potential across a selected pair of pins 38 that extend into cell growth media held in a well 16. FIG. 5 is a block diagram in accordance with the preferred embodiment of the present invention depicting a portion of the electronic circuit for applying the potential across a pair of pins 38 and for monitoring cultured cells. The computer program executed by the computer system (omitted from FIG. 5) included in the cell culture monitoring and recording system disclosed in those patent applications causes a programmable gain amplifier 42 included in a data acquisition board 44 to transmit a voltage representative of the voltage applied across a pair of pins 38 inserted into a well 16 for digitization by a measurement input/output board 46. The measurement input/output board 46 of the present embodiment is preferably a MetraByte DAS-8 Data Acquisition and Control Board marketed by Keithley Metrabyte Corporation of Taunton, Mass.

To supply the alternating current voltage that is applied across a selected pair of pins 38, the data acquisition board 44 includes a programmable voltage source 48. The programmable voltage source 48 includes an alternating current generator 52 that produces a 370 Hz ±20%, 10 volt peak-to-peak sine wave signal. The output signal produced by the alternating current generator 52 is transmitted to a programmable attenuator 54 also included in the programmable voltage source 48. Digital excitation level control signals supplied from the computer system to the programmable attenuator 54 via excitation level control signal lines 56 permit adjustment of the peak-to-peak voltage of the alternating current supplied to a first terminal 57 of a 20.04K ohm resistor 58. As disclosed in the patent applications identified above, a second terminal 59 of the resistor 58 connects to a bank of switches 62. One of the switches 62 is selected by the computer system, as disclosed in the patent applications identified above, for applying the alternating current voltage supplied by the programmable voltage source 48 to a pair of pins 38 that extend into the well 16 being monitored.

In accordance with the disclosure of the patent applications identified above, the alternating current voltage applied across a pair of pins 38 is also supplied to the input of the programmable gain amplifier 42. As described in the patent applications, the gain of the programmable gain amplifier 42 may be adjusted by control signals supplied from the computer system via gain control signal lines 64. The output signals from the programmable attenuator 54, and from the programmable gain amplifier 42 are both supplied to a multiplexer 66. Control signals supplied from the computer system to the multiplexer 66 via multiplexer control signal lines 68 select one of these three signals for application to an input of a sample-and-hold amplifier 70 included in the measurement input/output board 46. The output signal from the sample-and-hold amplifier 70 is supplied to the input of an analog-to-digital converter 72 also included in the measurement input/output board 46.

In addition to being supplied to the programmable attenuator 54, the 10 volt peak-to-peak output signal from the alternating current generator 52 is also supplied to the input of a comparator 74. The output signal from the comparator 74 changes state each time the alternating current voltage produced by the alternating current generator 52 passes through zero volts. Thus, while the alternating current voltage produced by the generator 52 has a potential greater than zero volts, the output signal from the comparator 74 is in one state, and while that voltage has a potential less than zero volts, the output signal from the comparator 74 is in its other state. The output signal from the comparator 74 is supplied to a programmable timer 76 included in the measurement input/output board 46.

Determining Delay Period

While the peak-to-peak voltage produced by the alternating current generator 52 remains satisfactorily constant throughout several days of a test, the frequency of its output signal is much less stable. Determining the electrical conductivity between a pair of pins 38 with sufficient accuracy while applying only a 10 millivolt potential across the pins 38 requires that the output signal from the programmable gain amplifier 42 be sampled by the sample-and-hold amplifier 70 precisely at the instant that the voltage supplied to the first terminal 57 of the resistor 58 reaches its maximum value. Because the frequency of the alternating current voltage may change over time, it has proven beneficial to the accurate and repeatable operation of the cell culture monitoring and recording system to adjust the instant at which the sample-and-hold amplifier 70 samples the output signal from the programmable gain amplifier 42 to match the frequency of the alternating current voltage produced by the programmable voltage source 48.

Figure 6:
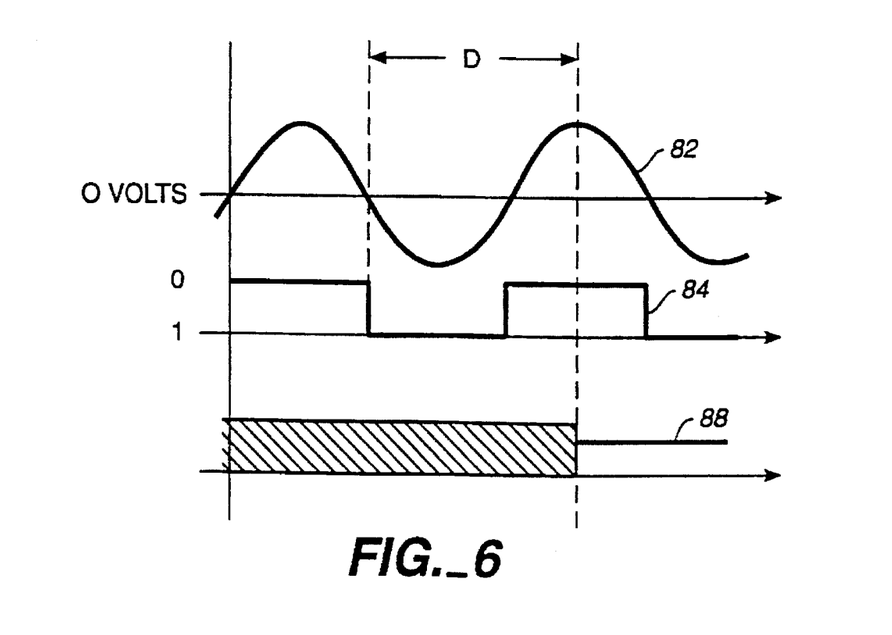
FIG. 6 depicts waveforms for the alternating current voltage supplied for application across a pair of pins, an output signal produced by a comparator in response to the alternating current voltage, and a hypothetical output signal from a sample-and-hold amplifier.

FIG. 6 depicts a sinusoidal alternating current waveform 82 for the voltage present at the output of the alternating current generator 52 together with the a digital waveform 84 of the output signal produced by the comparator 74. During initialization of the cell culture monitoring and recording system and at any subsequent time that it is requested by an operator of the cell culture monitoring and recording system, the computer program executed by the computer system executes a procedure for establishing a delay period ("D"), illustrated in FIG. 6, beginning at the instant at which the sine waveform 82 in changing from a positive potential to a negative potential has a potential of zero volts, and the instant at which the sine waveform 82 has its immediately subsequent maximum positive value.

In measuring the delay period D, the computer program uses the output signal from the comparator 74 in the data acquisition board 44 together with the programmable timer 76 included in the measurement input/output board 46 to determine the duration of one period of the sine waveform 82. The computer program then establishes the delay period D at three-fourths of one period of the sine waveform 82. Having determined a proper delay period D, the computer program then loads that delay period into the programmable timer 76 so that all subsequent measurements of the electrical potential across a pair of pins 38 will occur precisely at the instant that the voltage supplied to the first terminal 57 of the resistor 58 reaches its maximum value.

In measuring the voltage applied across a pair of pins 38, the programmable timer 76 begins measuring each delay period at the instant at which the sine waveform 82 in changing from a positive potential to a negative potential has a potential of zero volts, i.e. immediately after the digital value of the output signal from the comparator 74 supplied to the programmable timer 76 changes from 0 to 1. When the delay period D expires, the programmable timer 76 immediately causes the sample-and-hold amplifier 70 to sample and hold the voltage of the signal supplied from the output of the programmable gain amplifier 42 via the multiplexer 66 as illustrated in the waveform 88 depicted in FIG. 6. The programmable timer 76 also causes the analog-to-digital converter 72 to convert the voltage of the analog signal received from the sample-and-hold amplifier 70 into a digital number. Subsequently, as described in the patent applications identified above, this digital number is transferred from the measurement input/output board 46 to the computer system for storage as raw data suitable for subsequent analysis and graphic display.

Adjusting Voltage Applied Across a Pair of Pins 38

After the program executed by the computer system determines the present duration to be used for the delay period D when monitoring cell cultures, it then prepares the alternating current voltage to be applied from the second terminal 59 of the resistor 58 across a pair of pins 38 during such monitoring. To prepare this alternating current voltage, the computer program first adjusts the programmable attenuator 54 so a potential of approximately 10 millivolts is present at its output and at the first terminal 57 of the resistor 58. Because the 20.04K ohm resistance of the resistor 58 separates its first terminal 57 from its second terminal 59, and because any cell growth media held in the well 16 provides some electrical conductivity between the pair of pins 38 inserted therein, initially the voltage at the second terminal 59 and across a pair of pin 38 must be less than the value of 10 millivolts intended to be used in measuring the conductivity between a pair of pins 38. The computer program then causes the multiplexer 66 to select the output signal from the programmable gain amplifier 42 for application to the input of the sample-and-hold amplifier 70, sets the gain of the programmable gain amplifier 42 so a peak voltage of 10 millivolts at the second terminal 59 of the resistor 58 will result in the analog-to-digital converter 72 producing a digital number that is approximately 83.3% of the full range of the analog-to-digital converter 72, and causes the bank of switches 62 to select a pair of pins 38 for application of the alternating current voltage.

Using the previously determined delay period D and the measurement input/output board 46, the cell culture monitoring and recording system then measures the peak alternating current voltage present at the second terminal 59 of the resistor 58 that is applied across the pair of pins 38. If the voltage at the second terminal 59 and across the pair of pins 38 is less than 5 millivolts, the computer program doubles the alternating current voltage produced by the programmable attenuator 54 repeatedly until the voltage measured at the second terminal 59 exceeds 5 millivolts. Having thus applied and measured an alternating current voltage across the pair of pins 38 that exceeds 5 millivolts and knowing the setting for the programmable attenuator 54 which produces that voltage, the computer program then computes a new setting for the programmable attenuator 54 that will apply approximately a 10 millivolt alternating current voltage to the second terminal 59 and across the pair of pins 38, and then transmits control signals setting the attenuator 54 to the computed value.

Determining Conductivity of the Well 16

Having established the value for the alternating current voltage applied by the programmable attenuator 54 to the first terminal 57 of the resistor 58, the system is now prepared to monitor and record the electrical conductivity of the well 16. In measuring the conductivity of the well 16, the computer program first repetitively measures the voltage applied across the pair of pins 38 and at the second terminal 59 of the resistor 58. After collecting 16 successive values for this voltage, the computer program then computes an average of the 16 values using a box-car filter to obtain a single, average value for the voltage across the pair of pins 38. Using the single value of the voltage across the pair of pins 38, the value of the voltage supplied by the programmable attenuator 54 to the first terminal 57 of the resistor 58, and the resistance of the resistor 58; the computer program then computes the conductivity of the cell growth media and cells, if any, between the pair of pins 38.

Having determined the conductivity between the pair of pins 38 for this well 16, the computer program first stores the conductivity value for subsequent analysis and then proceeds to measure the conductivity between another pair of pins 38 extending into another well 16 in the laboratory tray 14. In determining the conductivity of each well, the cell culture monitoring and recording system uses the procedures set forth above of first adjusting the alternating current voltage applied across the pair of pins 38, and then measuring and averaging the voltage applied across the pair of pins 38 extending into the well 16. This adjusting of the applied voltage and determining of cell conductivity is repeated over and over until a conductivity has been determined and stored for all wells 16 in the laboratory tray 14.

Analyzing Conductivity of the Wells 16

As described in the patent applications identified above, at least one of the wells 16 in the laboratory tray 14 must be a reference well 16 that holds only cell culture media without cells. Furthermore, this reference well 16 must be specifically so identified to the analysis computer program because that program uses the conductivity value for the reference well 16 in analyzing the conductivity for all the other wells 16.

In the patent applications identified above, analysis of the conductivity of a well 16 that held both cell growth media and cells included dividing the conductivity measured for the reference well 16 by the conductivity measured for the well 16 that held both the cell growth media and cells. Rather than using the electrical conductivity of the reference well 16 as the numerator of a fraction in analyzing the conductivity of a well that holds both cell growth media and cells, it has been found more advantageous in analyzing the conductivity of wells 16 holding both cell growth media and cells to subtract the conductivity determined for the reference well 16 from the conductivity determined for the well 16 holding both cell growth media and cells. Subtracting the conductivity measured for the reference well 16, i.e. a well that holds only cell growth media without cells, from the conductivity measured for wells 16 that holds both growth media and cells removes the electrical conductivity of the cell growth media from the data for such wells 16. Removing the cell growth media conductivity from the data for the wells 16 results in data values for the wells 16 holding both cell growth media and cells that more closely represents the electrical conductivity of only the cells themselves, and the cells' metabolic products.

Industrial Applicability

While the preferred embodiment of the present invention as described above employs a sinusoidal alternating current in monitoring cell cultures, it may be possible to employ any periodic voltage waveform that is symmetric about zero volts in determining conductivity between a pair of pins 38. Thus, for example, a system for monitoring and recording cell cultures in accordance with the present invention could employ an alternating current voltage having a triangular waveform.

Since a triangular waveform alternating current voltage may be easily generated using a digital logic circuit, in a system employing such a waveform it would be unnecessary to directly measure, as described above, the delay period D. Rather the digital circuits used in generating the triangular waveform alternating current voltage could themselves directly produce signals for controlling the operation of the sample-and-hold amplifier 70 and the analog-to-digital converter 72. However, such a system for monitoring and recording cell cultures would merely employ a different, well known technique for determining the delay period for its alternating current voltage that is equal to an interval of time between the alternating current voltage having an instantaneous potential of zero volts and having an instantaneous potential equal to the maximum voltage of the alternating current voltage.

The system for monitoring and recording cell cultures of the present invention may be used for nondestructively measuring the kinetics of cell growth. It may also be used to measure the response kinetics of target cell populations to hormones, growth factors, growth inhibitors, cytotoxins, and drugs that perturb cellular metabolism. This system for monitoring and recording cell cultures is particularly useful in areas such as anticancer drug screening. Conventional screening methods measure culture response following a fixed incubation time. Chemotherapeutic drugs which exhibit delayed action are often falsely identified as being inactive, while drugs which act very quickly may be indistinguishable from more slowly acting compounds. In comparison with conventional colorimetric endpoint assays, by making a sequence of measurements over an extended period of time the disclosed system for monitoring and recording cell cultures allows longer assay durations to identify drugs which exhibit a delayed effect, while also identifying drugs that act more rapidly.

Although the present invention has been described in terms of the presently preferred embodiment, it is to be understood that such disclosure is purely illustrative and is not to be interpreted as limiting. Consequently, without departing from the spirit and scope of the invention, various alterations, modifications, and/or alternative applications of the invention will, no doubt, be suggested to those skilled in the art after having read the preceding disclosure. Accordingly, it is intended that the following claims be interpreted as encompassing all alterations, modifications, or alternative applications as fall within the true spirit and scope of the invention.

What is claimed is:

1. A method for electronically monitoring and recording cells being cultured in a laboratory tray having a plurality of separate wells, each of the plurality of separate wells adapted for holding a quantity of cell growth media in which cells may be cultured, the method comprising the steps of:
   a. providing a laboratory tray having a plurality of separate wells, each of the wells adapted for holding a quantity of cell growth media in which cells may be cultured;
   b. disposing a pair of electrically conductive, elongated pins respectively through an open end of each of the wells in the laboratory tray to extend into cell growth media held therein;
   c. supplying an alternating current voltage for selective application across a pair of the electrically conductive, elongated pins for electronically monitoring and recording cells being cultured in the laboratory tray;
   d. prior to selecting a pair of the electrically conductive, elongated pins for application of the alternating current voltage, determining a delay period for the alternating current voltage equivalent to an interval of time between the alternating current voltage having an instantaneous potential of zero volts and having an instantaneous potential equal to the maximum voltage of the alternating current voltage; and
   e. upon selecting a pair of electrically conductive, elongated pins for application of the alternating current voltage, measuring electrical conductivity between the pair of electrically conductive, elongated pins, at a point where the alternating current voltage reaches a maximum voltage, said point being set by said delay period.

2. The method of claim 1 wherein the alternating current voltage has a symmetrical waveform and the delay period equals to three-fourths of one period of the alternating current voltage.

3. The method of claim 2 wherein the alternating current voltage applied across said pair of said electrically conductive, elongated pins has a frequency less than 1000 Hz.

4. The method of claim 2 wherein the alternating current voltage applied across said pair of said electrically conductive, elongated pins has a frequency that is not harmonically related to 60 Hz.

5. The method of claim 2 wherein the alternating current voltage applied across said pair of said electrically conductive, elongated pins has a frequency between 300 and 400 Hz.

6. The method of claim 5 wherein the alternating current voltage applied across said pair of said electrically conductive, elongated pins has a frequency that is not harmonically related to 60 Hz.

7. The method of claim 1 further comprising the step of providing a lid that includes a cover adapted to be positioned over the laboratory tray to block open ends of the plurality of separate wells in the laboratory tray; a printed circuit board secured to a top surface of the cover, the printed circuit board having a plurality of individual electrically conductive traces formed on a surface thereof; and a plurality of pin sockets equal in number to the plurality of individual electrically conductive traces formed on the printed circuit board, one of the pin sockets being electrically coupled and secured to each of the individual electrically conductive traces formed on the printed circuit board, each of the pin sockets receiving one of the electrically conductive, elongated pins.

8. The method of claim 7 wherein each of said pin sockets form a gas-tight engagement with said electrically conductive, elongated pin retained therein.

9. The method of claim 7 wherein the pin sockets included in the lid do not extend into cell growth media held in the plurality of separate wells.

10. The method of claim 7 wherein said plurality of electrically conductive, elongated pins are made from a non-reactive, electrically conductive material.

11. The method of claim 10 wherein said plurality of electrically conductive, elongated pins are made from stainless steel.

12. The method of claim 7 wherein one electrically conductive, elongated pin of every pair is electrically connected to a common potential.

13. The method of claim 1 further comprising the steps of:
   e. selecting a first pair of electrically conductive, elongated pins inserted into a reference well that holds only cell growth media without cells for application of the alternating current voltage;

f. measuring the electrical conductivity between the first pair of electrically conductive, elongated pins inserted into the reference well;

g. selecting a second pair of electrically conductive, elongated pins inserted into a well that holds cell growth media containing cells for application of the alternating current voltage;

h. measuring the electrical conductivity between the second pair of electrically conductive, elongated pins inserted into the well holding cell growth media containing cells; and i. subtracting the electrical conductivity measured for the reference well from the electrical conductivity measured for the well holding cell growth media containing cells.

14. The method of claim 1 wherein the alternating current voltage supplied is initially less than a pre-established target value intended to be used in measuring the electrical conductivity between the pair of electrically conductive, elongated pins, the method further comprising the steps of:

e. measuring the alternating current voltage applied across the pair of electrically conductive, elongated pins;

f. increasing the magnitude of the alternating current voltage applied across the pair of electrically conductive, elongated pins until it is approximately equal to the pre-established target value; and g. measuring the electrical conductivity between the pair of electrically conductive, elongated pins.

15. The method of claim 14 wherein the alternating current voltage applied across said pair of electrically conductive, elongated pins is less than 90 millivolts.

16. The method of claim 15 wherein the alternating current voltage applied across said pair of electrically conductive, elongated pins is less than 50 millivolts.

17. The method of claim 16 wherein the alternating current voltage applied across said pair of electrically conductive, elongated pins is less than 20 millivolts.

18. A method for electronically monitoring and recording cells being cultured in a laboratory tray having a plurality of separate wells, each of the plurality of separate wells adapted for holding a quantity of cell growth media in which cells may be cultured, the method comprising the steps of:

a. providing a laboratory tray having a plurality of separate wells, each of the wells adapted for holding a quantity of cell growth media in which cells may be cultured;

b. disposing a pair of electrically conductive, elongated pins respectively through an open end of each of the wells in the laboratory tray to extend into cell growth media held therein;

c. supplying an alternating current voltage for selective application across a pair of the electrically conductive, elongated pins for electronically monitoring and recording cells being cultured in the laboratory tray, the alternating current voltage initially being less than a pre-established target value intended to be used in measuring the electrical conductivity between the pair of electrically conductive, elongated pins;

d. selecting a pair of electrically conductive, elongated pins inserted into a well for application of the alternating current voltage:

e. measuring the voltage applied across the pair of electrically conductive, elongated pins;

f. increasing the magnitude of the alternating current voltage applied across the pair of electrically conductive, elongated pins until it is approximately equal to the pre-established target value; and g. measuring the electrical conductivity between the pair of electrically conductive, elongated pins.

* * * * *